US012653487B2

(12) United States Patent
Rebolj

(10) Patent No.: US 12,653,487 B2
(45) Date of Patent: Jun. 16, 2026

(54) DEVICE FOR MONITORING PHYSIOLOGICAL DATA AND SYSTEM COMPRISING SUCH DEVICE

(71) Applicant: Ravnovesje d.o.o., Medvode (SI)

(72) Inventor: Klemen Rebolj, Medvode (SI)

(73) Assignee: Ravnovesje d.o.o., Medvode (SI)

( * ) Notice: Subject to any disclaimer, the term of this patent is extended or adjusted under 35 U.S.C. 154(b) by 571 days.

(21) Appl. No.: 17/644,318

(22) Filed: Dec. 14, 2021

(65) Prior Publication Data

US 2022/0183654 A1 Jun. 16, 2022

(30) Foreign Application Priority Data

Dec. 15, 2020 (EP) ..................................... 20214244

(51) Int. Cl.
| | |
|---|---|
| *A61B 7/04* | (2006.01) |
| *A61M 21/02* | (2006.01) |
| *G16H 40/67* | (2018.01) |
| *H04R 1/46* | (2006.01) |
| *A61M 21/00* | (2006.01) |

(52) U.S. Cl.
CPC .............. *A61B 7/04* (2013.01); *A61M 21/02* (2013.01); *G16H 40/67* (2018.01); *H04R 1/46* (2013.01); *A61M 2021/0027* (2013.01); *A61M 2021/005* (2013.01); *A61M 2230/04* (2013.01)

(58) Field of Classification Search
CPC ....................................................... A61B 7/04
See application file for complete search history.

(56) References Cited

U.S. PATENT DOCUMENTS

| | | | |
|---|---|---|---|
| 2009/0060215 A1 | 3/2009 | Ocasio | |
| 2010/0240945 A1 | 9/2010 | Bikko | |
| 2010/0256529 A1 | 10/2010 | Grasing et al. | |
| 2013/0116513 A1* | 5/2013 | Smith .................... | G16H 40/63 |
| | | | 600/301 |
| 2014/0155762 A1* | 6/2014 | Maskara ................. | A61B 7/04 |
| | | | 600/528 |
| 2016/0317117 A1* | 11/2016 | Mason ..................... | A61B 7/04 |
| 2018/0184916 A1 | 7/2018 | Leboeuf et al. | |
| 2018/0317875 A1* | 11/2018 | Khayrullaev ........ | A61B 5/7221 |
| 2019/0069088 A1* | 2/2019 | Seiler ..................... | H04R 1/025 |
| 2019/0192015 A1* | 6/2019 | Campo ................ | A61B 5/6824 |
| 2019/0239819 A1* | 8/2019 | Chang .................... | A61B 7/003 |
| 2021/0345934 A1* | 11/2021 | Landgraf ............... | A61B 5/318 |
| 2023/0293103 A1* | 9/2023 | Higuchi ................. | G16H 15/00 |
| | | | 600/586 |

FOREIGN PATENT DOCUMENTS

WO      2008/097008 A1      8/2008

* cited by examiner

*Primary Examiner* — Benjamin J Klein
*Assistant Examiner* — Willow Grace Welch
(74) *Attorney, Agent, or Firm* — Vorys, Sater, Seymour and Pease LLP

(57) ABSTRACT

Provided is a digital stethoscope capable of outputting a heart sound data and/or a therapeutic data. The digital stethoscope includes a housing, a physiological data acquisition unit configured to acquire the heart sound data, a therapeutic data unit providing the therapeutic data and an output unit configured to output heart sound data and/or therapeutic data, wherein the physiological data acquisition unit and the therapeutic data unit are provided within the housing.

18 Claims, 6 Drawing Sheets

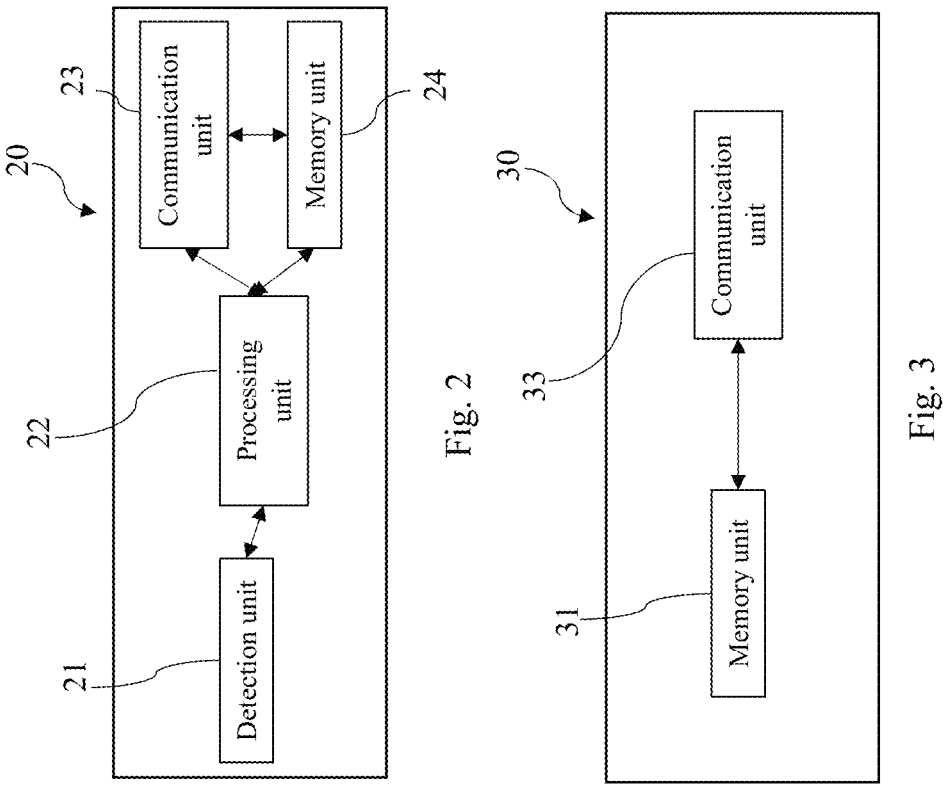
Fig. 2
Fig. 3
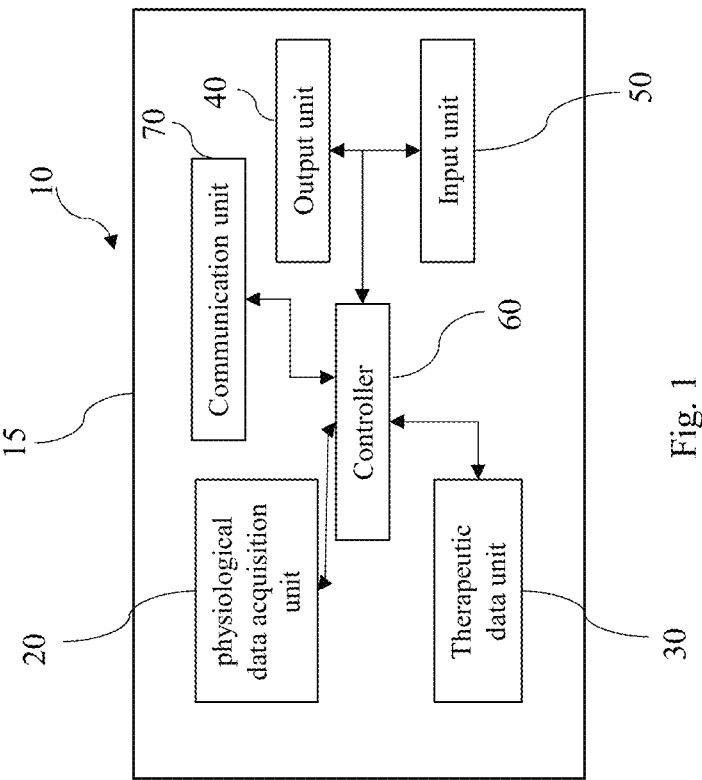
Fig. 1

Figures 5A, 5B:
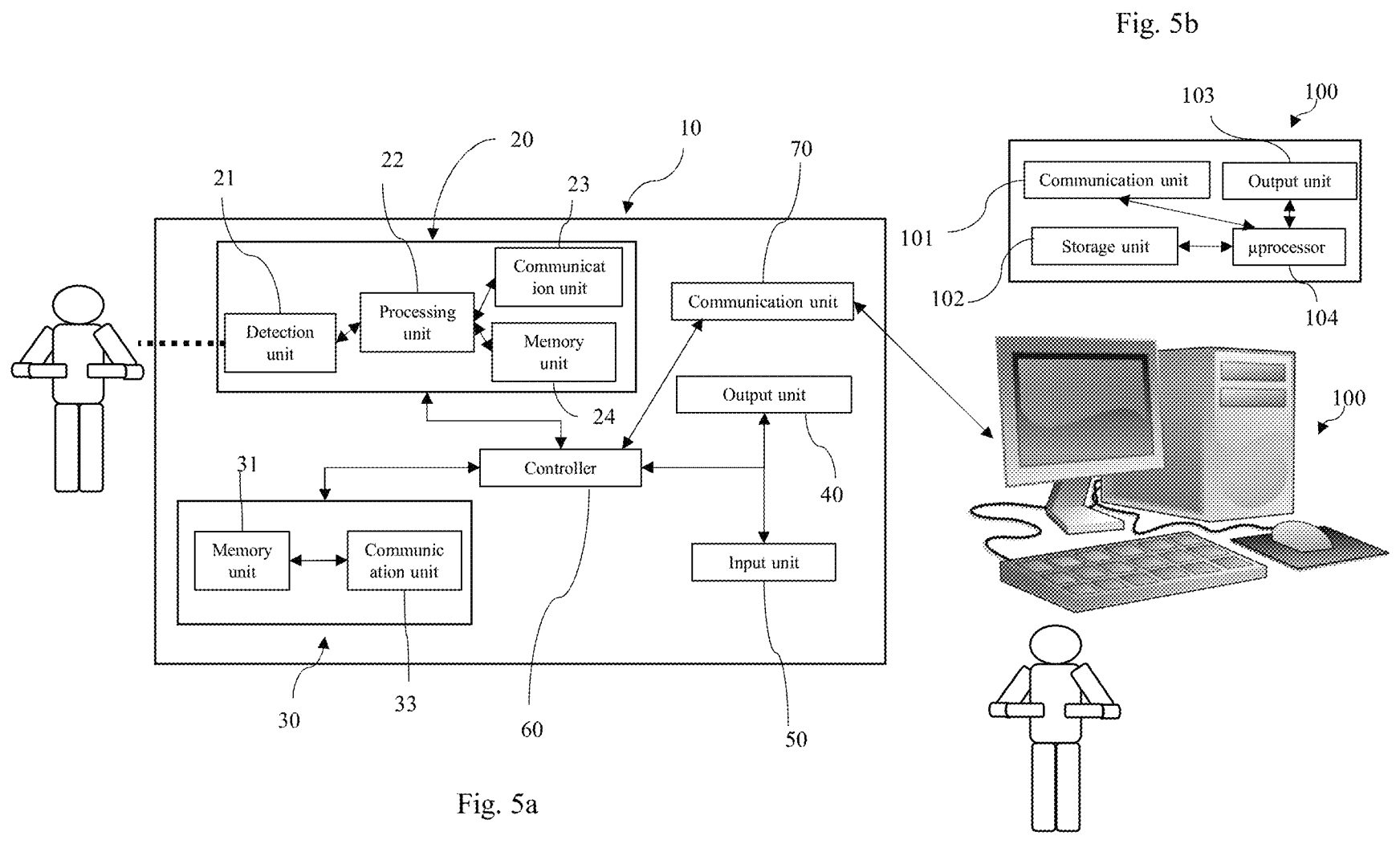

Output unit

μprocessor

104

Communication unit

Storage unit

Communication unit

70

10

Output unit

40

Input unit

50

Communicat ion unit

23

Memory unit

24

Controller

60

20

Processing unit

22

Detection unit

21

Communic ation unit

33

Memory unit

31

30

| Mental state | Therapeutic data |
|---|---|
| Mental Focus (Simple task) | Therapeutic audio + text 1 |
| Psychological Incoherence (Anger) | Therapeutic audio + text 2 |
| Relaxation | Therapeutic audio + text 3 |
| Psychological Coherence (Appreciation) | Therapeutic audio + text 4 |

TMS&PPm1

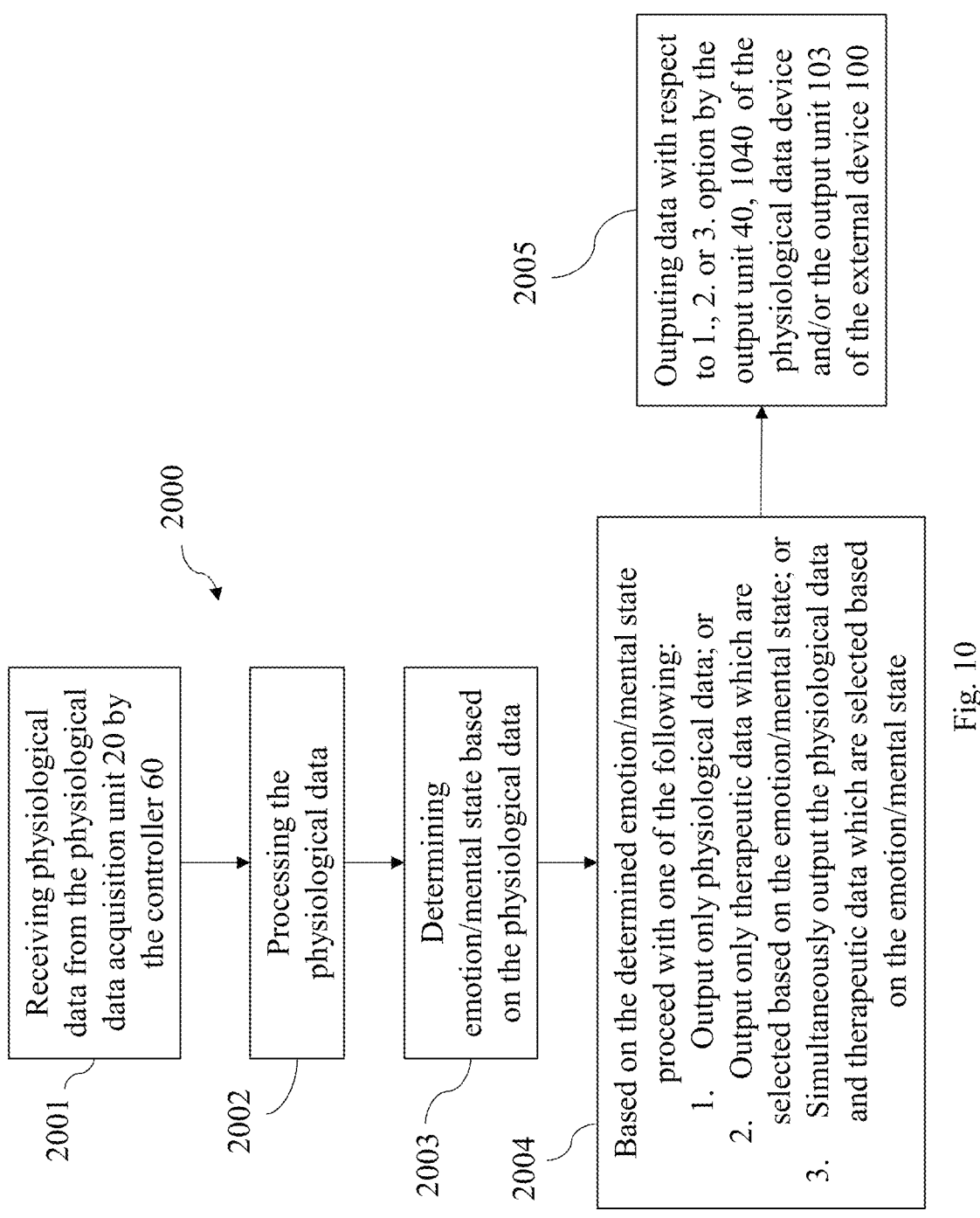

2001 Receiving physiological data from the physiological data acquisition unit 20 by the controller 60

2002 Processing the physiological data

2003 Determining emotion/mental state based on the physiological data

2004 Based on the determined emotion/mental state proceed with one of the following:
 1.   Output only physiological data; or
 2.   Output only therapeutic data which are selected based on the emotion/mental state; or
 3.   Simultaneously output the physiological data and therapeutic data which are selected based on the emotion/mental state 2005 Outputing data with respect to 1., 2. or 3. option by the output unit 40, 1040 of the physiological data device and/or the output unit 103 of the external device 100

DEVICE FOR MONITORING PHYSIOLOGICAL DATA AND SYSTEM COMPRISING SUCH DEVICE

TECHNICAL FIELD

The present invention relates to a device for monitoring physiological data or to a medical device capable of acquiring physiological or physiological data of a patient and for providing therapeutic data and outputting at least therapeutic data, more preferably also outputting the physiological data. Furthermore, it relates to a system comprising such device. Finally, it relates to a method for monitoring physiological data.

BACKGROUND ART

Devices for monitoring physiological data, which might called also medical devices, are used for monitoring a medical or physiological state of a patient. Such devices include devices for performing an electroencephalography (EEG), electrocardiography (ECG) and blood pressure measurements. Other physiological data monitoring or medical devices are used for diagnostic purposes. For example, medical imaging machines such as ultrasound, MRI (Magnetic resonance imaging) machines or and CT (Computer tomography) scanners are utilized in diagnosing a medical condition of a patient. Another example of diagnostic devices are auscultation systems such as conventional and digital stethoscopes, which are traditionally applied for listening to the heart sound, lung sound, fetal heart sound, bowel sound and pulse sound. Many of these devices can be connected to an external device such that data can be transferred from the physiological data monitoring device to the external device.

US 2009/0060215 A1 discloses a portable stethoscope for digitally recording heart sound and for transferring the heart sound to a computer system. The stethoscope comprises a USB port for communicating with a computer system. Head-phones enable a medical practitioner to digitally hear the patient sounds.

WO 2008/097008 A1 provides a wireless auscultation system using a multi-function digital stethoscope in which auscultation data of a patient collected through the digital electronic stethoscope are transmitted wirelessly by a transmitter to a separate speaker or a headset. In that case, an extra communication wire from the stethoscope to the speaker or the headset is not needed and so the stethoscope can be used free.

Such conventional physiological data monitoring devices serve either as aid devices in diagnosis or in monitoring or in life or fitness support or in treatment of medical conditions. They might be also applied in the wellness area. Hence, conventional physiological data monitoring devices are usually used only as a diagnostic aid or a treatment aid, thus providing only the physiological data.

Also, conventional devices are unable of automatically providing other data, like therapeutic treatment data to a patient based on his/her medical or physiological condition, without previous manual settings by a medical worker.

Thus, a necessity has appeared to provide a physiological data monitoring device capable of providing a physiological data and/or a therapeutic data, and hence being capable of providing a diagnostic and/or a therapeutic-treatment function. Further, the necessity has appeared to provide a physiological data monitoring device capable of providing therapeutic data based on the physiological data.

Technical Object

It is an object of the present invention to provide a physiological data monitoring device having the ability to be used as a physiological state deterministic device and a treatment device.

Another object of the present invention is to provide a physiological data monitoring device configured to acquire a physiological data of a patient and to provide therapeutic data or wellness data or fitness data.

Another object of the present invention is to provide a device configured to output physiological data or therapeutic data or both.

Another object of the present invention is to provide a physiological data monitoring device providing therapeutic data without assistance of a medical worker.

Another object of the present invention is to provide a physiological data monitoring device providing therapeutic data based on a state of a patient or user, preferably on a physiological or psychological state of a user.

Another object of the present invention is to provide a device determining if the device is in an appropriate position for correctly acquiring physiological data.

A further object is to provide a system comprising such device and a method using the device for improving the feeling of the user.

SUMMARY OF THE INVENTION

The objects of the present invention are solved by the features of the independent claims. Preferred embodiments are given in the dependent claims.

The general idea of the invention is to provide a physiological data monitoring device being able to provide the user or patient with data which is acquired by the device. This data could be in its simplest form the physiological data, which is acquired by the physiological data monitoring device.

An idea underlying the invention is that the physiological data provided to the user or the patient serve as therapeutic data to thereby induce a beneficial therapeutic effect on the user or the patient. In that way the acquired physiological data are used in improving the condition or wellbeing state of the user. Even more, to increase the therapeutic or wellbeing effect, the physiological data can be concurrently output with some other therapeutic data. By combining the acquired physiological data with therapeutic or any other data a synergistic effect can be achieved, which might be higher than the induced effect of physiological data or therapeutic data alone. Specifically, the inventive idea is to use heartbeat sound as physiological data to achieve psychophysiological coherence and well-being.

Emotional states of a person are inseparable with his/her heart rate and its variability. There are known examples of how different emotional states differently reflect on the heart rate and its variability and so the emotional state of a person can be successfully recognized or at least derived from the heartbeat. More surprisingly, the heart rate and its variability also influence an emotional state of a person. This so-called two-way heart-brain communication is also known as a connection between a psychophysiological and a cardiac coherence. Hence, by stimulating a psychophysiological coherence and well-being also a cardiac coherence is stimulated and vice-versa. In this example, the idea of the present invention is to stimulate the psychophysiological coherence and well-being by listening to physiological data, preferably the own heartbeat sound. As the psychophysiological coherence increases, also the cardiac coherence of the heartbeat sound automatically increases. In addition, the increased cardiac coherence further increases the psychophysiological coherence. Thereby, the psychophysiological and cardiac coherence mutually and intermittently enhance each other. In such a positive loop the time needed for achieving psychophysiological and cardiac coherence can be exponentially reduced. Even more, the time for achieving psychophysiological and cardiac coherence can be even additionally reduced by concurrently listening to other therapeutic data which are based on current emotional/mental state or heart sound.

So, a physiological data monitoring device is provided comprising: a housing, a physiological data acquisition unit configured to acquire a physiological data, and an output unit configured to output physiological data or any other data related to the physiological data.

Preferably, the physiological data monitoring device further comprises a therapeutic data unit providing a therapeutic data.

Preferably, the physiological data acquisition unit and the therapeutic data unit are provided within the housing.

A physiological data monitoring device of the present invention comprises a housing, a physiological data acquisition unit configured to acquire a physiological data, a therapeutic data unit providing a therapeutic data and an output unit configured to output physiological data and/or therapeutic data, wherein the physiological data acquisition unit and the therapeutic data unit are provided within the housing.

In an example the physiological data monitoring device may further comprise a controller being connected to at least one of the physiological data acquisition unit, to the therapeutic data unit and to the output unit. The controller may be configured to receive at least one of physiological data and therapeutic data. Further, the controller may be configured to process at least one of physiological data and therapeutic data. In addition, the controller may be configured to output at least one of the physiological data and therapeutic data.

In another example, the physiological data monitoring device may further comprise a communication unit configured to receive and/or transfer at least one of physiological data and/or therapeutic data from or to an external device.

Preferably, the physiological data monitoring acquisition unit may comprise a detection unit. Furthermore, it may comprise a processing unit. Next, the detection unit may be configured to detect the physiological data and the processing unit may be configured to process the physiological data. Preferably, the physiological data acquisition unit may comprise a communication unit configured to transfer physiological data to an external device. In some cases the physiological data acquisition unit may include a memory unit for storing at least part of the physiological data. In its simplest form the physiological data acquisition unit may include a sensor sensing physiological data, e.g. heart data, which are directly output to the controller of the physiological data monitoring device.

In another example, the physiological data acquisition unit may be simply a sensor configured to sense some physiological data. The sensor may be a piezoelectric sensor and/or a microphone and/or a membrane.

In another example, the physiological data monitoring device may be configured to determine whether the physiological data monitoring device is in an appropriate position for acquiring physiological data. Preferably, the physiological data monitoring device may be configured to first determine whether the physiological data monitoring device is in an appropriate position for acquiring the physiological data and based on determination that the physiological data monitoring device is in the appropriate position, start acquiring the physiological data.

In another example, the physiological data monitoring device may be configured to acquire a signal including the physiological data. Further, the physiological data monitoring device may be configured to determine a signal value of the acquired signal. Next, the physiological data monitoring device may be configured to compare the determined signal value of the acquired signal with a predetermined threshold value. Preferably, if the determined signal value of the acquired signal is higher than the predetermined threshold value, the physiological data monitoring device may be configured to determine that the medicals device is in an appropriate position for acquiring the physiological data and/or may be configured to output a control signal indicating that the physiological data monitoring device is in an appropriate position for acquiring physiological data. Alternatively, if the determined signal value of the acquired signal is lower than the predetermined threshold value, the physiological data monitoring device may be configured to determine that the physiological data monitoring device is not in the appropriate position for acquiring the physiological data and/or may be configured to output a control signal indicating that the physiological data monitoring device is not in an appropriate position for acquiring physiological data.

In another example, the physiological data monitoring device may be further configured to start acquiring the physiological data, after it has been determined that the physiological data monitoring device is in an appropriate position for acquiring physiological data.

In another example, when the physiological data monitoring device is not in the appropriate position for acquiring the physiological data, the physiological data monitoring device is configured to output a signal comprising positioning instructions on how to position the physiological data monitoring device to achieve an appropriate position for acquiring the physiological data. Preferably, the positioning instruction are based on an acquired signal comprising physiological data.

In another example, the physiological data monitoring device may be configured to determine whether the physiological data monitoring device is in the appropriate position for acquiring the physiological data based on determining a maximum signal of the physiological data from a plurality of signals of the physiological data at a plurality of different positions. Preferably, the physiological data monitoring device may be configured to first acquire a plurality of signals from a plurality of different positions and afterwards determine a maximum signal from the plurality of signals acquired from the plurality of different positions. More preferably, the physiological data monitoring device may be configured to further compare the determined maximum signal with a predetermined threshold value. Next, the physiological data monitoring device may be configured to based on the comparison between the determined maximum signal and the predetermined threshold value determine if the physiological data monitoring device is in appropriate position for acquiring the physiological data. Preferably, the physiological data monitoring device may be configured to compare a value of the determined maximum signal with the predetermined threshold value and if the value of the determined maximum signal is higher than the predetermined threshold value, the physiological data monitoring device may be configured to determine to be in the appropriate position for acquiring the physiological data. On the other hand, if the value of the determined maximum signal is lower than the predetermined value, the physiological data monitoring device may be configured to determine not to be in the appropriate position for acquiring the physiological data.

In another example, when the physiological data monitoring device has determined to be in the appropriate position for acquiring the physiological data, the physiological data monitoring device may be configured to release a control signal indicating that the physiological data monitoring device is in the appropriate position for acquiring the physiological data. Preferably, the physiological data monitoring device may be configured to release the control signal indicating that the physiological data monitoring device is in the appropriate position for acquiring the physiological data through the output unit of the physiological data monitoring device. Also, the control signal indicating that the physiological data monitoring device is in the appropriate position for acquiring the physiological data may be an audio signal and/or a video signal and/or a vibration signal. Following the control signal indicating that the physiological data monitoring device is in the appropriate position for acquiring the physiological data, the physiological data monitoring device may be configured to output a signal indicating that acquiring of the physiological data can start. The signal indicating that acquiring of the physiological data may start can be an audio and/or a video signal and/or a vibration signal. The signal may be output through the output unit of the physiological data monitoring device.

In another example, after the physiological data monitoring device has determined that the physiological data monitoring device is not in the appropriate position for acquiring the physiological data, the device may be configured to release a control signal indicating that the physiological data monitoring device is not in the appropriate position for acquiring the physiological data. Preferably, the physiological data monitoring device may be configured to release the control signal through the output unit of the physiological data monitoring device. Further, the control signal may be an audio signal and/or a video signal and/or vibration signal and the signal may be output through the output unit of the physiological data monitoring device. Next, the control signal indicating that the physiological data monitoring device is not in the appropriate position for acquiring the physiological data may be a different signal than the control signal indicating that the physiological data monitoring device is in the appropriate position for acquiring the physiological data.

In another example, after outputting the signal indicating that the physiological data monitoring device is not in the appropriate position for acquiring the physiological data, the physiological data monitoring device may be configured to output a signal comprising positioning instructions on how to position the physiological data monitoring device, such that the physiological data monitoring device will be eventually put in the appropriate position for acquiring the physiological data. The positioning instructions may comprise general instructions being independent from an acquired signal of the physiological data. Alternatively, the signal comprising instructions on how to position the physiological data monitoring device may comprise position-based instructions, which are based on an acquired signal of the physiological data. The position-based instructions may include instruction for positioning the physiological data monitoring device in direction of a positive gradient of the acquired signal of the physiological data in successive steps. Further, the position-based instructions may guide a user to position the physiological data monitoring device in the appropriate position for acquiring the physiological data after performing a plurality of positioning guiding steps following a positive gradient of the acquired signal of the physiological data.

In another example, a method for controlling the physiological data monitoring device may include acquiring a signal containing the physiological data. Further, the method may include determining a signal value from the acquired signal. Also, the method may include comparing the determined signal value from the acquired signal with a predetermined threshold value. Preferably, the method may include outputting a control signal indicating that the physiological data monitoring device is in an appropriate position for acquiring physiological data if the determined signal value is higher than the predetermined threshold value. Even more preferably, the method may include outputting a control signal indicating that the physiological data monitoring device is not in an appropriate position for acquiring physiological data if the determined signal value is lower than the predetermined threshold value.

In another example, the method may further comprise acquiring the physiological data after outputting the control signal for indicating that the physiological data monitoring device is in the appropriate position for acquiring physiological data.

In another example, the method may further comprise outputting a signal comprising positioning instructions on how to position the physiological data monitoring device to achieve an appropriate position for acquiring physiological data, when the physiological data monitoring device is not in an appropriate position for acquiring the physiological data. Preferably, the positioning instruction are based on an acquired signal comprising physiological data.

In another example, following the control signal indicating that the physiological data monitoring device is in the appropriate position for acquiring the physiological data, the method may include outputting a signal indicating that acquiring of the physiological data can start.

In another example, the method for controlling the physiological data monitoring device may further comprise acquiring a plurality of signals of the physiological data at a plurality of different positions, determining a maximum signal from the plurality of signals of the physiological data at the plurality of different positions, comparing the maximum signal from the plurality of signals of the physiological data with a predetermined threshold value, based on the comparison between the determined maximum signal and the predetermined threshold value determining whether the physiological data monitoring device is in an appropriate position for acquiring the physiological data. Preferably, the method for controlling the physiological data monitoring device may comprise comparing a value of the determined maximum signal with the predetermined threshold value and if the value of the determined maximum signal is higher than the predetermined threshold value, determining that the physiological data monitoring device is in an appropriate position for acquiring the physiological data. Otherwise, if the value of the determined maximum signal is lower than the predetermined threshold value, determining that the physiological data monitoring device is not in an appropriate position for acquiring the physiological data.

In another example, the method for controlling the physiological data monitoring device may further comprise: after determining that the physiological data monitoring device is not in the appropriate position for acquiring the physiological data outputting a signal comprising instruction on how to position the physiological data monitoring device, such that the physiological data monitoring device will be eventually positioned in the appropriate position for acquiring the physiological data. The signal comprising instructions on how to position the physiological data monitoring device may comprise general instructions being independent from an acquired signal of the physiological data. Alternatively, the signal comprising instructions on how to position the physiological data monitoring device may comprise position-based instructions, which are based on an acquired signal of the physiological data. The position-based instructions may include instruction for positioning the physiological data monitoring device in direction of a positive gradient of the acquired signal of the physiological data in successive steps. Further, the position-based instructions may guide a user to position the physiological data monitoring device in the appropriate position for acquiring the physiological data after performing a plurality of positioning guiding steps following a positive gradient of the acquired signal of the physiological data.

The physiological data may comprise a heart sound data. The physiological data may also comprise a lung sound data. The physiological data may also comprise a vein pulse sound data. Also, the physiological data may comprise a fetal heart sound data. Further, the physiological data may comprise bowel sound data. Also, the physiological data may comprise a blood pressure data and/or a blood consistence data. Next, the physiological data may comprise a respiratory data. Alternatively, the physiological data may comprise a urine consistence data and/or a gastrointestinal motility data.

In another example, the therapeutic data unit may comprise a memory unit for storing the therapeutic data. Also, the therapeutic data unit may comprise a communication unit capable of transmitting therapeutic data to an external device. More, the communication unit may be capable of receiving the therapeutic data from the external device.

In an example, the therapeutic data may comprise a therapeutic text. Also, it may comprise a therapeutic audio. Further, the therapeutic data may comprise therapeutic images or a therapeutic video. Also, the therapeutic data may comprise a therapeutic instruction. Even more, the therapeutic data may include a proposal of a medical treatment or actions for improving the wellbeing. Preferably, the therapeutic data comprises a combination thereof. The output of therapeutic data might be split, so some of the data might be output on the device itself, whereas other data might be display on connected display. So when providing either the physiological data or even the derived therapeutic data to an external device, like a server, the server might recognize which video data are suited to be display based on the received data and may then play these video data. So the user might listen to some data via the device, but might also watch video displayed by a website of a service provider.

In another example, the housing of the physiological data monitoring device may comprise a bottom portion, a middle portion provided on the bottom portion and may comprise a top portion provided on the middle portion.

In another example, a radius of the bottom portion may be greater than a radius of the top portion. Further, a radius of the upper part of the middle portion may be smaller than a radius of the lower part of the middle portion. Preferably, the middle portion is formed as a bell shape. The parts of the housing of the device are functionally distributed, So at the bottom part there is the heart sound receiver (acquiring unit), in the middle there is the processing unit, on which the software for processing the acquired data is executed. Furthermore, buttons, touch buttons, and/or sockets and lamps might be placed at any suitable location at the housing. The top portion might comprise a control screen and/or the output devices, like loudspeakers or display. The control screen might be a touch screen for receiving inputs of the user and outputting video data or images.

In another example, the housing might have a neck-shaped portion, which may be provided between the middle portion and the top portion. Further, the neck-shaped portion may have a smaller radius than the upper radius of the middle portion. This facilitates the handling of the device.

In another example, the physiological data acquisition unit may be provided in the bottom portion. Optionally, the physiological data acquisition unit may be connected to the bottom portion.

In another example, the top portion may comprise a flat portion being substantially parallel to the bottom surface.

In another example, the therapeutic data unit may be provided in the middle portion. Further, the top portion may comprise an input unit. Additionally, the top portion may comprise an output unit.

In another example, the output unit may be further configured to output physiological data and/or therapeutic data.

In another example, the controller may be configured to select therapeutic data for being output at least based on physiological data acquired by the physiological data acquisition unit. Further, the controller may be configured to select therapeutic data for being output at least based on data input by a user or based on a combination of a user input and the acquired data.

In another example, the output unit may be further configured to output the therapeutic data via a loudspeaker. Alternatively or additionally, it may be configured to output the therapeutic data via an earphone. It may also be configured to output the therapeutic data via a display. Also, the output unit may be configured to output the physiological data via a loudspeaker. Preferably, it may be configured to output the physiological data via an earphone. More preferably, it may be configured to output the physiological data via a display. It might be also possible to output the physiological data via a haptic output unit. Thus the user might feel its physiological data.

In another example, the physiological data and the therapeutic data may be simultaneously output by the output unit. This improves the therapeutic effect.

In an example, the therapeutic data may be output by the output unit before the physiological data is output. Alternatively, the physiological data may be output by the output unit before the therapeutic data is output. By this sequence of outing the data, the user might be better prepared or adapted to recognize the physiological or therapeutic data.

In an example, the physiological data monitoring device is included in a system further comprising an external device communicating with the physiological data monitoring device. The external device may further comprise a communication unit configured to communicate with the physiological data monitoring device. The external device may also comprise a storage unit for storing the therapeutic data. Further, the external device may comprise an output unit for outputting the therapeutic data. Preferably, the storage unit of the external device may store the physiological data. Even more preferably, the output unit of the external device may output the physiological data. Therapeutic audio texts might be streamed or transferred to the device from a server or personal computer and might optionally remain in the device, which might be also called or realised as a digital stethoscope. In principle, the sound of the heartbeat or heart tones (physiological data) will not be provided to the external device, like a personal computer. The user should always listen only to his current heart rhythm and not to any recordings of his heartbeat received from outside or an external device.

In another example, the output unit of the external device may be configured to output or transfer the therapeutic data based on the physiological data.

In another example, the external device may simultaneously output the therapeutic and the physiological data.

In another example, the output unit of the external device may be further configured to output the therapeutic data via a loudspeaker. Further, it may be configured to output the therapeutic data via an earphone. It may also be configured to output the therapeutic data via a display. Also, the output unit of the external device may be configured to output the physiological data via a loudspeaker. Preferably, it may be configured to output the physiological data via an earphone. More preferably, it may be configured to output the physiological data via a display. A playing and/or analyzing of heart tones on a computer might be useful for any consulting people, likes doctors or medical worker communicating with the patient.

In an example, the therapeutic data is output before the physiological data by the output unit of the external device.

In another example, the physiological data is output before the therapeutic data by the output unit of the external device.

In another example, the physiological data monitoring device may be a digital stethoscope.

In another example, the therapeutic data may be transferred from the external device to the physiological data monitoring device. Especially, the therapeutic data may be transferred from the external device to the therapeutic data unit. Preferably, the therapeutic data may be transferred from the storage unit of the external device to the memory unit of the therapeutic data unit. In particular, the therapeutic data may be transferred from the storage unit of the external device to the memory unit of the therapeutic data unit via the communication unit of the external device and the communication unit of the therapeutic data unit.

In another example, the therapeutic data may be transferred from the physiological data monitoring device to the external device for storing or further processing. However, basically, therapeutic audio texts (therapeutic data) will be transferred or streamed from a computer or from a website of a server to the physiological data monitoring device or digital stethoscope. In particular, the therapeutic data may be transferred from the memory unit of the therapeutic data unit to the storage unit of the external device via the communication unit of the therapeutic data unit and the communication unit of the external device.

In another example, the physiological data may be transferred from the physiological data monitoring device to the external device. Preferably, the physiological data may be transferred from the physiological data acquisition unit to the external device. Especially, the physiological data may be transferred from the memory unit of the physiological data acquisition unit to the storage unit of the external device. Preferably, the physiological data may be transferred from the memory unit of the physiological data acquisition unit to the storage unit of the external device via the communication unit of the physiological data acquisition unit and the communication unit of the external device.

In another example, the therapeutic data output by the physiological data monitoring device and/or the external device may be selected based on the physiological data. Also, the therapeutic data output by the physiological data monitoring device and/or the external device may be selected independently of the physiological data. Further, the therapeutic data output by the physiological data monitoring device and/or the external device may be selected by a user. So, before listening to his own heart, the user may also determine the parameters of listening to therapeutic audio texts. Further, the therapeutic data output by the physiological data monitoring device and/or the external device may be selected or influenced by a third person having access to or who is monitoring the physiological data monitoring device and/or the external device.

In an example, the therapeutic data output by the physiological data monitoring device and/or the external device may be selected based on a health condition or medical condition represented by the physiological data. The condition may be determined based on the physiological data. Further, a plurality of therapeutic data may be selected for a medical condition. Preferably, one therapeutic data may be selected for a predetermined medical condition. Also, the physiological data monitoring device may be configured to select the therapeutic data based on the acquired physiological data. The external device may be configured to select the therapeutic data based on the physiological data. It is possible that during the time a user devotes to listening to her/his own heart, she/he only use a digital stethoscope (device). It is used by the personal computer (an external device) before and after a listening session to stream therapeutic audio texts and charge the battery of the device In another embodiment, the therapeutic data may be output from the physiological data monitoring device and/or the external device simultaneously with the physiological data only during particular medical condition. Hence, the physiological data monitoring device and/or the external device may output therapeutic data only during particular medical condition.

In an example, the external device may be a personal computer, an electronic portable device, a mobile telephone, a television, a projector, an external server or any other electronic device, capable of receiving, transferring, storing and outputting data.

In an example, the physiological data monitoring device may be connected to the external device through a wired connection. Also, the physiological data monitoring device may be connected to the external device through a wireless connection.

The object is also solved by a method for improving or enhancing or influencing the mental state of a user. The method comprises acquiring physiological data, analysing the physiological data and outputting the physiological and/or a therapeutic data based on the analysis.

The therapeutic data can be also defined as wellness data or relaxing data or motivation data.

Technical Advantage

A technical advantage of the physiological data monitoring device of the present invention is in its most advanced realization the concurrent provision of a physiological data and a therapeutic data.

The physiological data monitoring device can provide therapeutic data based on the physiological data and so improve the therapeutic effect achieved by the therapeutic data.

Further, by outputting the physiological data and the therapeutic data simultaneously or subsequently an advantageous synergistic therapeutic effect is achieved.

Also, by determining if the physiological data monitoring device is in an appropriate position for acquiring the physiological data an advantageous acquiring of physiological data is achieved.

LIST OF FIGURES

FIG. 1 is a schematic representation of a physiological data monitoring device.

FIG. 2 is a schematic representation of a physiological data acquisition unit of the physiological data monitoring device.

FIG. 3 is a schematic illustration of a therapeutic unit of the physiological data monitoring device.

FIG. 5a illustrates data communication between a physiological data monitoring device and an external device.

FIG. 5b illustrates components of the external device.

Figures 7A, 7B, 8, 9:
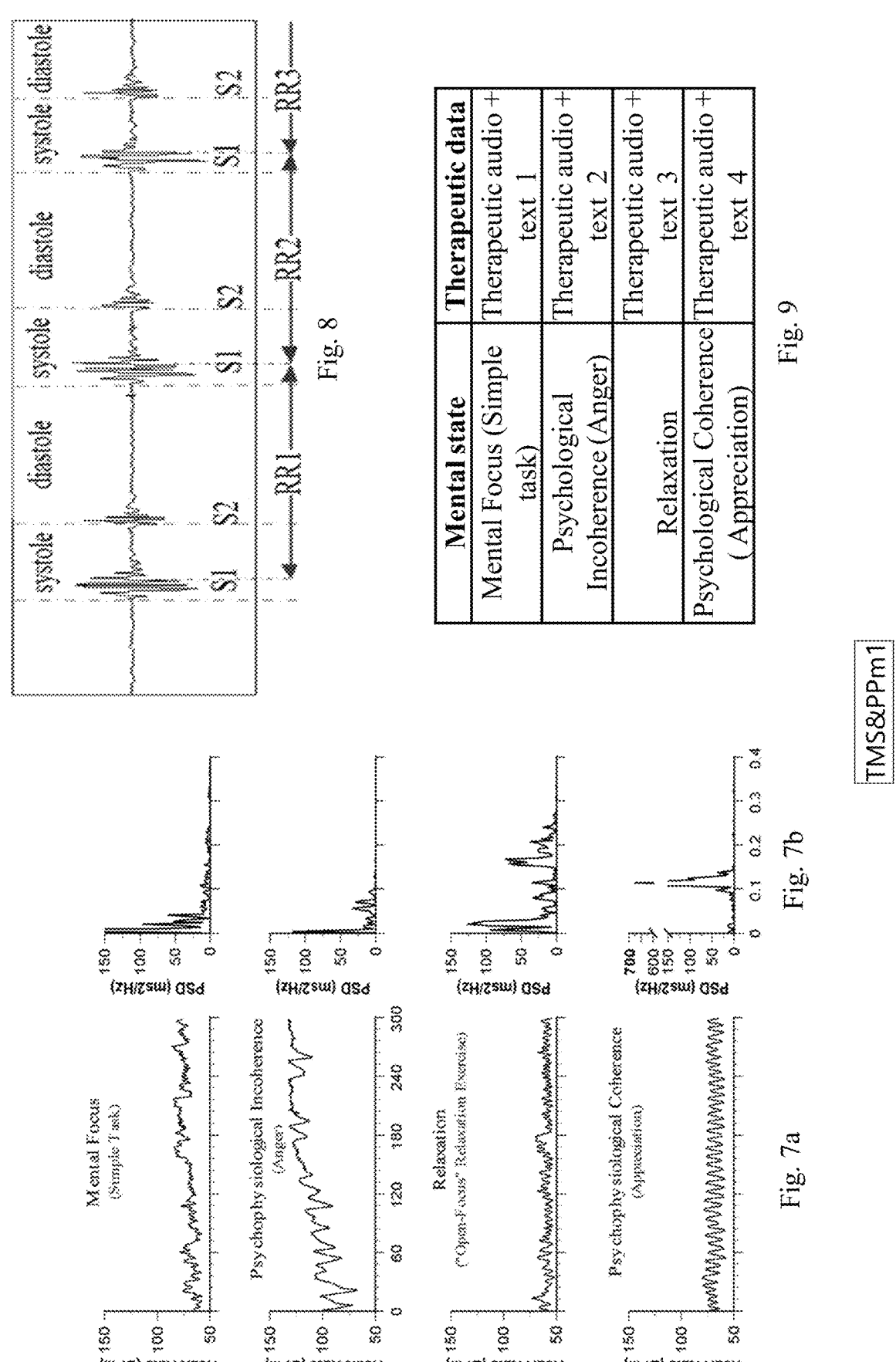

FIG. 7a demonstrates examples for heart rate data in different emotional/mental states.

FIG. 7b shows power spectral density graphs of the corresponding heart rate data of FIG. 7a.

FIG. 8 shows a typical sound signal comprising portions corresponding to a systolic and diastolic heart function.

FIG. 9 shows connection between an emotion/mental state and its corresponding therapeutic data.

FIG. 10 demonstrates a process of outputting data based on detected physiological data.

DETAILED DESCRIPTION

FIGS. 1-4 show a physiological data monitoring device 10 comprising a physiological data acquisition unit 20, a therapeutic data unit 30 and an output unit 40. The physiological data acquisition unit 20 is configured to acquire a physiological data from a patient. On the other hand, the therapeutic data unit 30 is configured to provide a therapeutic data. The output unit 40, however, is configured to output either physiological data or therapeutic data or both. The physiological data monitoring device 10 further comprises an input unit 50 configured to receive input data from a user or a patient, a controller 60 configured to control the output of medical and/or therapeutic data based on the input data received from the input unit 50 and a communication unit 70 for communicating with external devices. Also, the therapeutic data unit 30 is further configured to store therapeutic data and to provide therapeutic data to the controller 60. Based on the input data provided from the input unit 50, the controller 60 determines if the physiological data and/or the therapeutic data will be provided to the output unit 40 and be output therefrom.

Schematic diagram in FIG. 2 shows an example of the structure of the physiological data acquisition unit 20. In this example, the physiological data acquisition unit 20 comprises a detection unit 21, a processing unit 22, a communication unit 23 and a memory unit 24. The units are mutually connected, such that the detection unit 21 is directly connected to the processing unit 22, the communication unit 23 is directly connected to the processing unit 22 and to the memory unit 24, the memory unit 24 is directly connected to the processing unit 22 and to the communication unit 23, and the processing unit 22 is directly connected to each of these units. However, the physiological data acquisition unit 20 can be in its simple form only a sensor, e.g. a sound detecting sensor such as a microphone. Hence, the physiological data acquisition unit 20 may only comprise a sensing unit (not shown in the Figures) configured to sense the physiological data.

Next, regarding FIG. 2, the detection unit 21 of the physiological data acquisition unit 20 is configured to detect physiological data of a patient. Thereby the way of detection depends on the type of the physiological data. In case of detecting sound data, such as heart sound data, a lung sound data, a vein pulse sound data, a fetal heart sound data or a bowel sound data, or a combination thereof, the detecting unit 21 detects sound and transforms it into a digital signal. The sound is first detected by an electronic stethoscope sensor with commonly known transducers such as microphone, piezoelectric sensor, etc. In the next step the detected signal is amplified and filtered. Further, the amplified and filtered analog signal is converted to a digital signal by the analog-digital converter.

On the other hand, the processing unit 22 is configured to process the signal detected in the detection unit 21, such that the quality of the signal is improved. Hence, the detected, amplified and from analog to digital converted signal is from the detection unit 21 output to the processing unit 22. Therein a digital filter is used to extract the signal within a frequency band of interest from the noisy data, such that the signal-to-noise ratio of the signal is improved. Further, the improved signal is next normalized to a certain scale, so that the expected amplitude of the signal is not affected from the data acquisition locations and different samples.

From the processing unit 22, the signal is transferred to the memory unit 24, where it is stored. Hence, the detected, filtered, amplified and processed physiological data are so stored in the memory unit 24. When the stored physiological data are needed by the controller 60, the physiological data stored in the memory unit 24 are transferred from the memory unit 24 to the controller 60. In a special mode of action, the processed physiological data is not in-between stored in the memory unit 24 but is directly transferred from the processing unit 22 through the communication unit 23 to the controller 60.

In another embodiment, the physiological data acquisition unit 20 comprises only a sensing unit or sensor configured to sense the physiological data. In the embodiment, the physiological data sensed by the sensing unit or sensor are promptly transferred to the controller 60, wherein the physiological data are processed and stored. The sensing unit or sensor can be an electronic stethoscope sensor with commonly known transducers such as a microphone or a piezoelectric sensor.

Further, FIG. 3 depicts a detailed structure of the therapeutic data unit 30. The therapeutic data unit 30 comprises a memory unit 31 and a communication unit 33 is configured to receive therapeutic data from the memory unit 31 and if requested provide it to the controller 60. Hence, upon request from controller 60, the therapeutic data stored in the memory unit 31 can be transferred to the controller 60. The controller 60 can request the therapeutic data from the therapeutic data unit 30 based on input data provided by a user at the input unit 50. On the other hand, the therapeutic data unit can also receive therapeutic data from an external device and store them in the memory unit 31 of the therapeutic data unit 30. This pathway is in detail described in description of FIG. 5.

Figure 4:
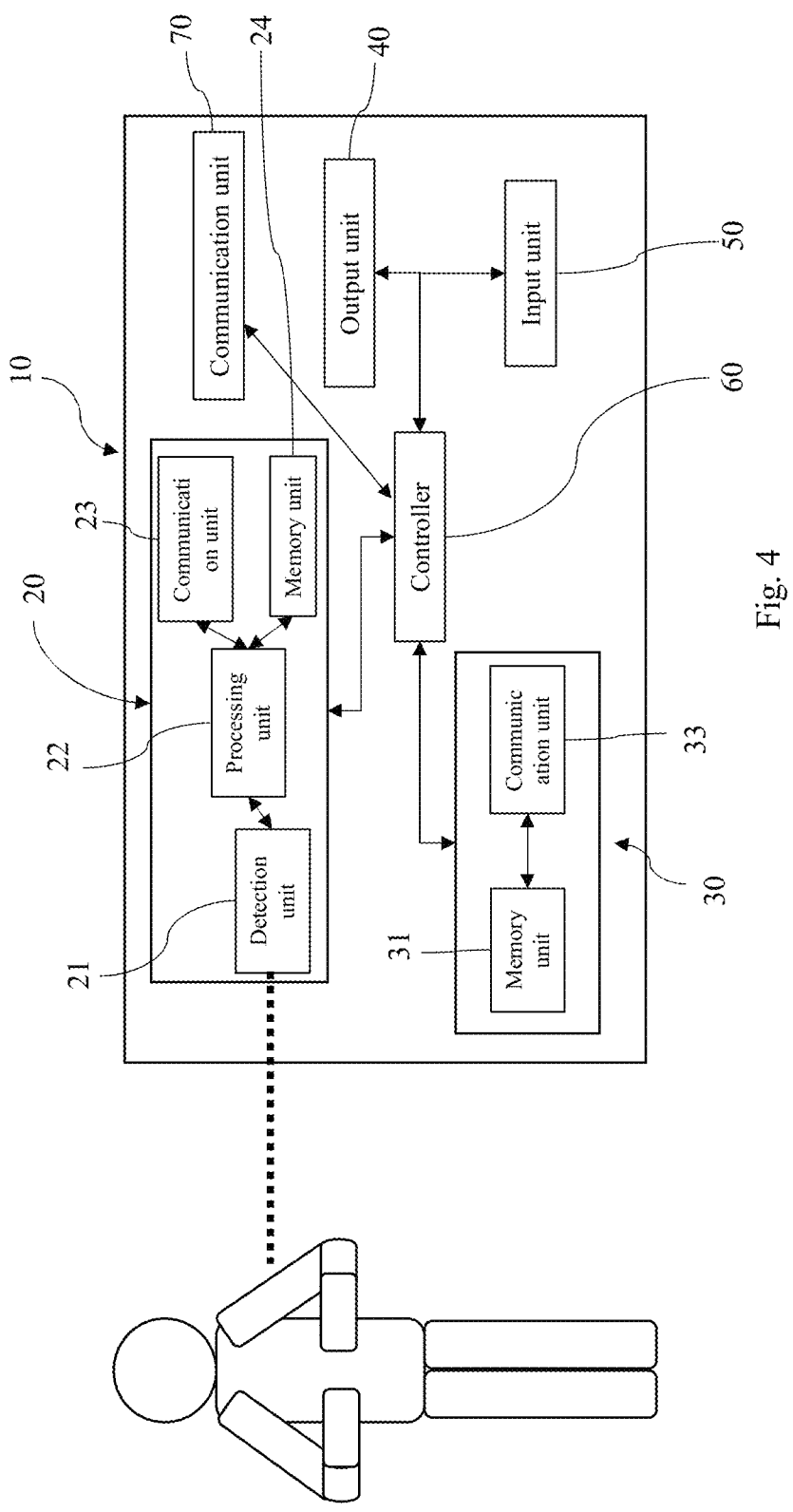
FIG. 4 is a schematic representation of a physiological data monitoring device.

FIG. 4 further depicts the physiological data monitoring device 10 comprising a physiological data acquisition unit 20, therapeutic data unit 30, an output unit 40, an input unit 50, a controller 60 and a communication unit 70. Further, the input 50 unit can be designed as a touchscreen, as a touchpad, as a mouse, as a keyboard and/or as a combination thereof. On the other hand, the output unit 40 can be designed as a display, as a screen, as a loudspeaker, as a projector, as a headset, as a headphone, and/or a combination thereof and/or as any other device capable of outputting audio and/or visual data. Also, the communication unit 70 is configured to enable a wired and/or a wireless connection to an external device. The wireless connection may include Wi-Fi, Bluetooth, radio communication, IR or near field communication and/or any other wireless communication presently known and/or a combination thereof.

Further, with respect to FIG. 4 the whole process from the user perspective from acquiring the physiological data to the outputting of the physiological data and/or the therapeutic data from the output unit 40 will be described. When the user decides to use the physiological data monitoring device, the user triggers acquiring of the physiological data by the physiological data acquisition unit 20 by inputting corresponding instructive input data in the input unit 50. Based on the input data, the controller 60 triggers the medical acquisition 20 unit to detect and acquire the physiological data from the user. As already described hereinabove, in an embodiment of the physiological data acquisition unit 20, the physiological data are first detected by a detection unit 21, being afterwards processed by the processing unit 22 and finally being stored in the memory unit 24. However, in another embodiment of the physiological data acquisition unit 20 in which the physiological data acquisition unit 20 only comprises a sensing unit or sensor, the acquired/sensed physiological data are upon acquiring/sensing promptly transferred to the controller 60, wherein they are processed and stored. Next, after the physiological data have been acquired and stored either in the memory unit 24 or in the controller 60, the user may further decide which physiological data stored in the memory unit 24 or in the controller 60 will be output from the output unit 40 and when. On that behalf the user provides the controller 60 with the corresponding command by inputting corresponding input data in the input unit 50. Additionally, the user may also choose in the output unit 40 to output the therapeutic data. Thereby the user may choose to output the therapeutic data concurrently with the physiological data or to output the therapeutic data after the physiological data, or to output the therapeutic data before the physiological data, or to output the physiological data and the therapeutic data intermittently with a particular frequency of taking turns. Moreover, the user can arbitrary select when and how to output the physiological data and the therapeutic data.

Thereby the user can select a particular portion of the therapeutic data from the whole set of therapeutic data stored in the memory unit 31. The therapeutic data comprise a set of therapeutic audios, therapeutic texts, therapeutic videos, therapeutic instructions and any other kind of audio and visual information which may advantageously affect a physical and/or a mental state of the user. Preferably, the user may choose to concurrently output the chosen physiological data and the chosen therapeutic data from the output unit 40.

In an example, the physiological data monitoring device 10 can be driven by only one person without needing an assistance from another person. In such case, a patient can acquire physiological data about his/her medical condition and discern them through the output unit 40 in form of visual and/or audio representation. Further, it can simultaneously discern also the therapeutic data output from the output unit 40. Alternatively, the device can be also used by a plurality of people, wherein physiological data are acquired by one person, wherein another person operates the physiological data monitoring device 10.

Next, FIG. 5 depicts an example of the present invention, wherein the physiological data monitoring device 10 can be connected to an external device 100, either through a wired or a wireless connection. The external device 100 comprises a communication unit 101 configured to be able to communicate with the communication unit 70 of the physiological data monitoring device. Further, the external device comprises a storage unit 102 for storing data, an output unit 103 and a microprocessor 104 for coordinating the function of the other units.

Further, FIGS. 5*a*, 5*b* illustrate how physiological data are acquired from the user/patient and how the physiological data and/or therapeutic data are output by the physiological data monitoring device 10 and/or the external device 100.

In an example of a function, the communication unit 101 of the external device 100 receives physiological data from the physiological data acquisition unit 20 via the controller 60 and via the communication unit 70 of the physiological data monitoring device and stores it at the storage unit 102 of the external device 100.

In another example, when the physiological data acquisition unit 20 comprises only the sensing unit or sensor, the communication unit 101 of the external device 100 receives physiological data from the controller 60 via the communication unit 70 of the physiological data monitoring device and stores it at the storage unit 102 of the external device 100.

In another example, the external device 100 also receives therapeutic data from the therapeutic data unit 30 via the controller 60, via the communication unit 70 of the physiological data monitoring device 10 and via the communication unit 101 of the external device 100 and stores it in the storage unit 102 of the external device. In another function, the microprocessor 104 of the external device 100 analyses the physiological data received from the physiological data monitoring device 10 and based on it determines a medical condition/state of the patient/user. Thereby the medical condition/state can be inherently connected with the physiological data. Next, the external device can simultaneously output the physiological data and the conclusions about the medical condition/state through the output unit 103. The output unit 103 of the external device 100 may be a display, a loudspeaker, a projector, a headphone and/or any other electronic unit capable of outputting visual and audio data, and/or a combination thereof.

Also, in another example the therapeutic data and the physiological data can be both transferred to the external device 100, being processed in the microprocessor 104 and being afterwards concurrently output from the output unit 103 of the external device 100 and/or stored.

In another example, the external device 100 may store the therapeutic data in the storage unit 102 and upon request from the physiological data monitoring device 10, the therapeutic data stored in the storage unit 102 can be transferred from the storage unit 102 to the memory unit 31 of the physiological data monitoring device 10. Afterwards, in the corresponding mode of action the therapeutic data can be afterwards further output by the output unit 40 of the physiological data monitoring device 10 as already explained above.

In an example, a person can operate the physiological data monitoring device 10 and the external device 100. Nevertheless, it is also possible, that one person operates the physiological data monitoring device 10, wherein another person operates the external device 100. Next, it is possible that physiological data are acquired with the physiological data monitoring device 10 from a first person, wherein a second person controls the physiological data monitoring device 10 while physiological data are acquired from the first person, and a third person operates the external device 100. For example, this would be a case, when the first person is a patient, the second person is a medical assistant and the third person is a physician.

Figure 6:
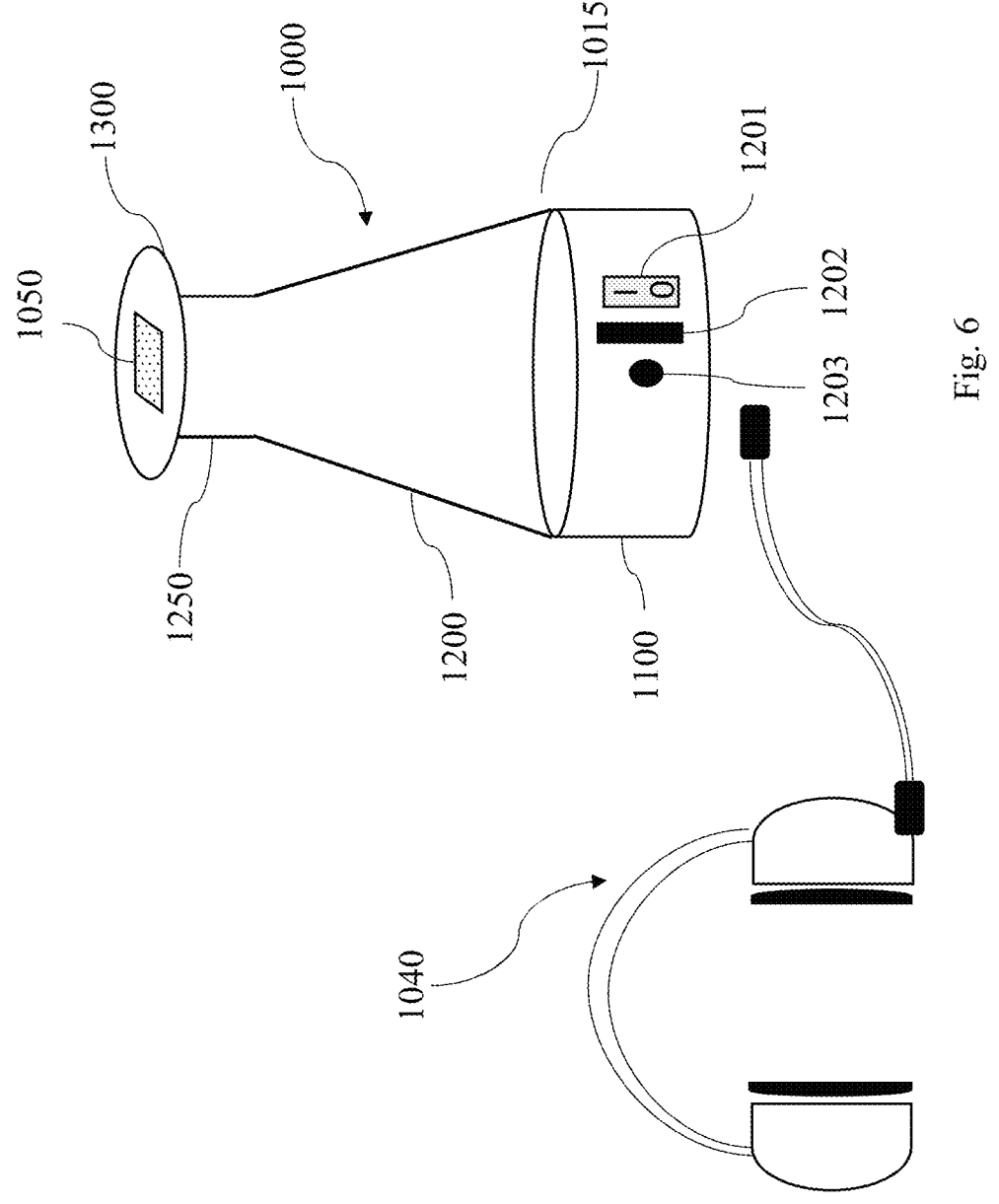
FIG. 6 shows an example of a digital stethoscope according to the present disclosure.

FIG. 6 shows an exemplary embodiment of the housing of the physiological data monitoring device 10 in form of a customized digital stethoscope 1000. The customized digital stethoscope 1000 comprises a housing 1015 including a round bottom portion 1100, a bell-shaped middle portion 1200 and a round top flat portion 1300.

The round bottom portion 1100 defines the most lower part of the digital stethoscope 1000, wherein the bell-shaped middle portion 1200 is provided above the round bottom portion 1100 and the round top flat portion 1300 is provided above of the bell-shaped middle portion 1200. Hence, the bell-shaped middle portion is provided between the round bottom portion 1100 and the round top flat portion 1300.

In the round bottom portion 1100 there is provided a physiological data acquisition unit comprising a tuneable diaphragm, digital microphone and a noise reduction technology configured for heart sound detection and processing. The radius of the round bottom 1100 is of about 3 cm.

The bottom rises into a bell-shaped middle portion shape 1200. In the bell-shaped middle portion 1200 electronic parts of the therapeutic data unit 30 and controller 60 are disposed. Also, the bell-shaped middle portion 1200 comprises a turn on/off switch 1201 of the digital stethoscope, a cable socket 1202 and a headphone socket 1203. By applying the turn on/off switch 1201, the digital stethoscope 1000 can be turned on or turned off, respectively. On the other hand, a charger cable can be input into the cable socket 1202 to charge the digital stethoscope 1000. The cable socket 1202 can be designed as an USB-port socket. In addition, the headphone socket 1203 serves as a connection socket through which the output unit 40, 1040 in form of wired and/or wireless headphones 1040 can be connected with a main body of the digital stethoscope 1000 defined by the housing 1015. The wireless headphones 1040 can be for example a Bluetooth headphones.

The top of the bell-shaped middle portion 1200 further continues into a neck 1250 having a height of about 1 cm. On the top of the neck 1250, there is provided the round flat plate 1300. The bell-shaped middle portion 1200 is configured in such shape that the radius of the bottom part being in contact with the round bottom portion 1100 is greater than the radius of the neck 1250. Further, the bell-shaped middle portion 1200 has such a shape, that its radius decreases from bottom to the top. Hence, the radius of the bell-shaped middle portion 1200 decreases from the bottom portion 1100 to the neck 1250. Specifically, the radius of the bell-shaped middle portion 1200 linearly decreases with the height from the bottom portion 1100 to the neck 1250.

On the top of the neck 1250 there is provided the round flat plate 1300. The round flat plate 1300 has a greater radius than the neck 1250, but a smaller radius than the bottom portion 1100. Hence, the round flat plate 1300 has also a smaller radius than the lower portion of the bell-shaped middle portion 1200. Next, the radius of the round flat portion approximately corresponds the radius of the middle part of the bell-shaped middle portion 1200. On the top of the round flat portion an input unit 50, 1050 in form of a touch screen 1050 is provided. The input unit 1050 in formed of a touch screen, allows the user to input the working instructions to the customized digital stethoscope 1000.

Next, an output unit 1040 in form of headphones 1040 is provided to the customized digital stethoscope 1000. Based on the input instructions provided by the user, the output unit 1040 can output the detected heart sound data and/or the therapeutic data stored tin the digital stethoscope 1000. The type of the sound data output from the output unit 1040 is based on the selection of the user in the input unit. The headphones 1040 presented in FIG. 6 can be also implemented as wireless headphones, such as e.g. Bluetooth headphones. Also, instead of the headphones 1040, the digital stethoscope 1000 may be connected to an external device 100 such as a mobile phone, computer, loudspeaker etc., which will be implemented as the output unit 1040. The external devices 100 will be connected to the digital stethoscope 1000 either wirelessly or through the USB port 1202 provided at the bell-shaped middle portion 1200.

In an example of use, the customized digital stethoscope 1000 can be used as follows. After switching on the digital stethoscope, the user defines desired operating parameters of the digital stethoscope 1000 on the touch screen 1050. The operating parameters include a selection if only the detected heart beat sound would be output or if only therapeutic data in form of audio texts would be output, or both together, selecting the volume of the output heart beat sound, selecting volume of the output audio therapeutic text, manual selection of a specific therapeutic text. Further, the user can also select an option in which the digital stethoscope 1000 automatically selects therapeutic text, volume of the output therapeutic text and volume of the output heart beat sound based on the properties of the detected heart sound. The working method of this option is described later on. After selecting the operating parameters, the user may plug in the headphones 1040 in the headphone socket 1203, lies down, places the round bottom portion 1100 of the stethoscope 1000 on the chest, such that the round bottom portion 1100 is in the contact with the chest and functions as heart sound data acquiring unit, places headphones 1040 in or on her/his ears and starts listening to his/her own heart beat sound, or a therapeutic audio text or to a combination of the his/her own heart beat sound and of the therapeutic audio.

In another example of use, the customized digital stethoscope 1000 can be additionally connected to an external device 100 such a mobile phone, an external server, a computer, a display by a wired and a wireless connection. In case of the wired connection, the external device 100 can be connected with the digital stethoscope by an USB cable, which is with its one end plugged into the external device 100, and with its other end plugged into the USB port 1202 provided at the bell-shaped middle portion 1200. The external device 100 can be used as an output unit 1040. However, the external device 100 can be also used for storing therapeutic texts and detected heart sound data. In a mode of such application the detected heart sound data can be transferred to the external device 100 through the USB or wireless connection and be output or be permanently stored on the external device 100. Further, the heart sound data can be further analysed at the external device for determining the medical condition of the user. On the other hand, the therapeutic texts can be also primary stored at the external device 100, and when the user may select some therapeutic texts on the external device 100 and upload them on the digital stethoscope 1000 through the wired or the wireless connection. In another application, the user can download therapeutic texts from the web and upload them to the digital stethoscope 1000.

FIGS. 7-10 show a special mode of the digital stethoscope 1000 in which the digital stethoscope 1000 automatically determines medical state of the user based on the acquired physiological data and based on the physiological data automatically selects and outputs therapeutic data, which should bring beneficial effect to the user/patient in a particular emotion/mental state. In this example, the physiological data comprise heart sound data and the medical state comprises different emotions or mental states in which the user/patient may find himself/herself. On the other hand, the therapeutic data comprise emotion/mental state specific therapeutic texts, emotion/mental state specific therapeutic music, emotion/mental state based volume of the output therapeutic text, and/or volume of the output therapeutic music, and/or volume of the output heart sound data.

FIGS. 7a, 7b show plots of a heart rate (in beats per minute (BPM)) vs. time of four basic emotions/mental states and their corresponding power spectral density (PSD) plots. In FIG. 7a, typical plots of a heart rate vs. time by emotions/mental states like Mental Focus, Psychophysiological Incoherence, Relaxation and Psychophysiological Coherence are provided. Correspondingly to these plots, the power spectral density (PSD) plots of these graphs are shown in FIG. 7b. The power spectral density (PSD) plots are generated from heart rate plots by performing a Fourier transform. Hence, the power density plot (PSD) holds information about probability or frequency of a heart frequency in the heart rate vs. time plot. The Fourier transform can be for example performed by applying a Fast Fourier Transform (FFT) or a Discrete Fourier transform (DFT). On the other hand, FIG. 8 demonstrates a typical signal of a heart sound data acquired by the physiological data acquisition unit 20. Each heart pulse comprises a first heart sound S1 and a second heart sound S2. The beginning of the first heart sound S1 characterizes a start of the systolic action and the beginning of the second heart sound S2 characterizes the start of the diastolic action. The length of a heartbeat $RR_i$ can thus be calculated as a time difference between two subsequent S1 sounds.

Further, emotion/mental state of a user/patient can be determined based on the data presented in FIGS. 7a, 7b and 8. FIG. 7a clearly demonstrates strong differences in heart sound data for different emotion/mental states. There are several possibilities and methods known in the prior art by which the emotion/mental state of the user can be determined.

In one example, emotion/mental state is determined based on the maximum peak of the power spectral density (PSD) plot within the frequency interval of [0.06 Hz, 0.30 Hz]. Thereby, a so-called coherence ratio $C_{ratio}$ is extracted. To calculate the coherence ratio $C_{ratio}$, first a maximum peak $f_{max}$ $(v_{max})$ is found in the range of $v \in$ [0.06 Hz, 0.30 Hz] of the power spectral density (PSD) plot f'(v). Secondly, the sum power $P_{max}$ of the peak $f_{max}$ $(v_{max})$ is calculated, by integrating power spectral density plot (PSD) f'(v) in the frequency interval of $v \in$ [$v_{max}$–0.05 Hz, $v_{max}$+0.05 Hz]. Beside that the total power $P_{total}$ of the range $v \in$ [0.06 Hz, 0.30 Hz] from which the maximum peak $f_{max}$ $(v_{max})$ was selected, is calculated. Finally, the coherence ratio $C_{ratio}$ is calculated by dividing $P_{max}$ with the $P_{total}$–$P_{max}$. Specific intervals of coherence ratios $C_{ratio}$ correspond to a specific emotion/mental state of a person. Hence, through calculation of the coherence ratio $C_{ratio}$ from a heart sound data, an emotional/mental state of a user can be determined. Based on this determination, the controller 60 selects specific therapeutic data as shown in FIG. 9. The therapeutic data of specific emotion/mental state may differ in therapeutic texts, audios and in volume of the output texts and audios.

In another example, determination of an emotion/mental state of a user may be based on his/her heart rate variability HRV. In this method, first a length of a heartbeat $RR_i$ is calculated for a plurality of heartbeats within some time interval and afterwards a variability of the lengths $RR_i$ of the heartbeats is calculated. This variability corresponds to the heart rate variability HRV. The heart rate variability HRV selectively corresponds to some emotion/mental state. There are several prior-art methods known by which the heart rate variability can be calculated. For example, in heartbeat lengths $RR_i$ can be calculated as time differences between two subsequent sounds S1 or as time differences between two subsequent sounds S2. On the other hand, heartbeat lengths $RR_i$ can be also calculated as normalized heartbeat lengths between two not subsequent S1 or S2 sounds. In this way, the normalized heartbeat length corresponds to a time difference between two not subsequent sounds S1 or sounds S2 divided by the number of sounds S1 or sounds S2 which lie between the two not subsequent sounds S1 or sounds S2. Regardless of the way in which the heart rate variability HRV is calculated, the heart rate variability HRV is a selective indicator for an emotion/mental state of a user/patient.

FIG. 10 demonstrates a process 2000 of the physiological data monitoring device 10 or specifically of the digital stethoscope 1000 of outputting data based on detected physiological data. Within the process the physiological data monitoring device 10 in form of the digital stethoscope 10, 1000 acquires physiological data in form of a heart beat sound, automatically determines emotion/mental state of a user based on the acquired heart sound data, and finally outputs physiological data and/or therapeutic data based on the determined mental state of the user. With the reference to FIG. 10 the process 2000 comprises the following subsequent steps.

First, the controller 60 of the physiological data monitoring device 10 receives 2001 physiological data from the physiological data acquisition unit 20. In the next step, the controller 60 processes 2002 the physiological data such that they are transformed into a form from which an emotion/mental state can be determined. Processing 2002 of the physiological data comprises in the first line filtering, and amplification of the detected physiological data such that its signal to noise ratio is increased. Next, the processing step 2002 also comprises analysis of the physiological data in form of extraction of critical features and parameters based on which an emotion/mental state of a user/patient can be determined. This analysis includes the hereinabove described methods of determining coherence ratio $C_{ratio}$ and heart rate variability HRV from the heart sound data, as also any other method for analysis of the physiological data and its connection to the physical/mental state of a user/patient.

After the processing 2002 of the physiological data an emotion/mental state of the user/patient is determined 2003 based on the processed physiological data. In this determination step 2003, the critical features of the physiological data such as coherence ratio $C_{ratio}$ and heart rate variability HRV are used to determine the emotion/mental state of the user. Based on the determined emotion/mental state, the controller 60 selects in the next step 2004 among three options on how to proceed. In the first option, the controller 60 determines based on the emotion/mental state to output only physiological data. In the second option however, the controller 60 determines which therapeutic data should be output based on the emotion/mental state and determines to output only the therapeutic data without outputting the physiological data. On the other hand, in the third option the controller 60 determines which therapeutic data should be output based on the emotion/mental state and determines to outputs the therapeutic data simultaneously with the physiological data.

According to one of the three options of the step 2004, the controller 60 next provides the corresponding physiological data and/or therapeutic data to the output unit 40 of the physiological data monitoring device 10, 1000 and/or the output unit 103 of the external device 100. Finally, the corresponding physiological data and/or therapeutic data is output 2005 by the output unit 40 of the physiological data monitoring device 10, 1000 and/or the output unit 103 of the external device 100.

The physiological data monitoring device 10 of the present invention may be also configured to determine whether the physiological data monitoring device 10, 1000 is positioned at an appropriate position during acquiring of the physiological data. In detail, when a user decides to acquire physiological data with the physiological data monitoring device 10, the user first brings the device to an approximate vicinity of the region where under normal/usual circumstances physiological data can be acquired. Hence, on the example of the physiological data monitoring device 10 being the digital stethoscope 10, 1000 used for listening to a heartbeat, the user first places the digital stethoscope 10, 1000 on the upper central portion of the thorax, hence in the known approximate vicinity of a heart. Thereby the digital stethoscope first detects if the digital stethoscope has been brought in juncture with the skin. If the digital stethoscope 10, 1000 determines that the digital stethoscope 10, 1000 has been brought in juncture with the skin, the digital stethoscope 10, 1000 outputs a first control signal indicating to the user that the digital stethoscope 10, 1000 has been brought in juncture with the skin. The first control signal can be output by the output unit 40 of the digital stethoscope 10, 1000, and the signal can be an audio signal, a video signal, a vibration signal, or any combination thereof. Concurrently with the outputting of the first control signal, the digital stethoscope 10, 1000 starts acquiring the physiological data—heart sound data according to the hereinabove description. The digital stethoscope 10, 1000 acquires the signal of the heart sound data by the physiological data acquisition unit 20, wherein the data are first detected by the detection unit 21, processed by the processing unit 22 and stored in the memory unit 24 or directly via the communication unit 23 provided to the controller 60 of the digital stethoscope 10, 1000. Next, from the processed heart sound data a signal value of the heart sound data is extracted in the controller 60 of the digital stethoscope 10, 1000. The signal value may be a sound amplitude, or an average sound intensity over a particular period of time, or an amplitude of the maximum peak in the power spectral density (PSD) graph of the heart sound signal, or a cumulative power calculated from a particular frequency interval in the power spectral density (PSD) graph, or any linear or nonlinear combination of these values or any other single values which may be extracted from a signal. Further, the determined signal value is compared with a predetermined threshold value saved in the controller 60 and if it is determined that the determined signal value is higher than the predetermined threshold value, the digital stethoscope 10, 1000 outputs a control signal indicating that the physiological data monitoring device is in an appropriate position for acquiring physiological data. The control signal can be output by the output unit 40 of the digital stethoscope 10, 1000 and can be an audio signal, a visual signal, a vibration signal or a combination thereof. Further, the control signal for indicating that the digital stethoscope 10, 1000 is in an appropriate position for acquiring physiological data is very different from the first signal indicating that the digital stethoscope 10, 1000 is in juncture with the skin, hence making it easily recognizable for the user that the digital stethoscope 10, 1000 is now positioned in the appropriate position for acquiring physiological data. Otherwise, if the determined signal value is lower than the predetermined threshold value, the digital stethoscope 10, 1000 outputs another control signal indicating that the digital stethoscope 10, 1000 is not in an appropriate position for acquiring hear sound data. The another control signal is also output by the output unit 40 of the digital stethoscope 10, 1000 and can be an audio signal, a visual signal, a vibration signal or a combination thereof, wherein the another control signal highly differentiates from the first signal indicating that the digital stethoscope 10, 1000 is in juncture with the skin, and form the control signal indicating that the digital stethoscope 10, 1000 is in an appropriate position for acquiring the heart sound data. Thus, from the first signal, the control signal and the another control signal the user can obviously recognize if the digital stethoscope 10, 1000 is or is not in juncture with the skin, and/or if the digital stethoscope 10, 1000 is in an appropriate position for acquiring the heart sound data and/or if the digital stethoscope 10, 1000 is not in an appropriate position for acquiring the heart sound data.

Further, if the digital stethoscope 10, 1000 is in the appropriate position for acquiring the heart sound data, the user will be informed by the corresponding signal that he/she can keep the digital stethoscope 10, 1000 at this position for a longer period of time. On the other hand, through the other signal indicating that the digital stethoscope 10, 1000 is not in the appropriate position, the user will be triggered to change the position of the digital stethoscope 10, 1000 to another place and wait for the next signal being output from the digital stethoscope 10, 1000. The next signal can be again a signal indicating that the digital stethoscope 10, 1000 is either in an appropriate or not appropriate position. Thereby, dependent on the signal the user may leave the stethoscope positioned at the place or again move it to another place, looking so long for the appropriate place until the appropriate place is found. Also, the time necessary for acquiring the heart sound data is between 1 s to 10 s, wherein the user guided not to move the digital stethoscope 10, 1000 from a particular position before a particular control signal is output.

In a mode of operation, when a user turns on the digital stethoscope 10, 1000, it is possible to set several options. A menu may appear on the touch screen 1050 or on the display based on which the user may select whether he/she wants to listen only to therapeutic data, or only to the heart sound data, or concurrently to both—the therapeutic data and the heart sound data.

When the user selects to listen only to the therapeutic data, another menu may appear presenting a list of all therapeutic data stored in the digital stethoscope 10, 1000. From the list of therapeutic data stored in the digital stethoscope 10, 1000, the user may select one of the therapeutic data. If the list of therapeutic data does not include therapeutic data the user wants to select, he might download more therapeutic data from the server or from the external device.

As the storage capacity of the digital stethoscope 10, 1000 limited it might happen that the user selects therapeutic data which is not locally stored in the digital stethoscope 10, 1000. So, he may download additional therapeutic audios, videos, texts and/or music from the server or from the external device. The digital stethoscope 10, 1000 is automatically connected to the server by a Wi-Fi connection, or by a wired connection, and so the controller 60 of the digital stethoscope 10, 1000 automatically checks if all therapeutic data available on the server are uploaded on the digital stethoscope 10, 1000, when the digital stethoscope 10, 1000 is turned on. In case that not all therapeutic data are present in the list, a menu may appear indicating that all therapeutic data will be automatically downloaded from the server.

The therapeutic audios, videos, texts and music provided in the list may be listed in three main categories. In a first category there is provided a list of therapeutic audios, videos, texts and/or music which enhance the current mental state of the person. In a second category there may be a list of therapeutic audios, videos, texts and music which help the user to relax or to activate, i.e. to change the mental state. In a third category there is a list of therapeutic audios, videos, texts and/or music, which may help the user to achieve a particular wanted mental state starting from an unknown, undefined or preferably any mental state.

Examples of therapeutic audios, videos, texts and/or music of the first category are the following. If the user is mentally focused and wants to enhance the metal focused state, he/she may select a therapeutic text comprising elements of classical music, nature sound reproducing music, such as rain sound, bird chirping, waterfall sound etc. Mental focusing music may also include cinematic background sounds and video game music. The therapeutic data reproduced if the user wants to stay in his current metal state may have a frequency or beats per minute, which correspond to the measured heart rate. Furthermore, such therapeutic data may include text modules suited to motivate the user such as "Focus!", "Stay focused!", "You can do it", "You own this" which might be played with particular repeating frequency.

On the other hand, if the user is in a relaxed state and wants to enhance it, therapeutic relaxation music can be played, like meditation music, natural sounds reproducing music, such as rain sound, bird chirping, waterfall sound. Further, the texts to improve the relaxed state might be inserted into the music, like "Relax", "Everything is fine", "Everything will be alright", "Slowly breathe in, slowly breathe out". The therapeutic data for this metal state may also include counting of seconds of breathing in and breathing out.

If the user is in a psychophysiological incoherence state the therapeutic data may include a combination of the music, audio texts, and videos of the therapeutic data for the mental focusing state and relaxed state. So, the aim is to bring the user into a psychophysiological coherence state. Here, a combination of therapeutic data as indicated above may be used, wherein the emphasis of each data is determined by the relative amount of time each therapeutic data is played. So, in that case the mental focusing data are played more often than relaxing therapeutic data in particular amount of time.

Alternatively, if the user is in a psychophysiological coherence the therapeutic data includes music, audio texts, and videos of the therapeutic data or a combination thereof for the mental focusing state and the relaxed state, wherein in that case the emphasis is on the relaxing therapeutic data.

In that case the relaxing therapeutic data are played more often than mental focusing data in a particular amount of time.

Examples of the therapeutic data in the second category comprise examples when the user is at the beginning of a mental focused state and wants to achieve a relaxed state or a psychophysiological coherence state. If the user wants to achieve the relaxed state the therapeutic data corresponds to the above described therapeutic data for enhancing the relaxed state, and if the user want to achieve a psychophysiological coherence state, the therapeutic data corresponds to the above described therapeutic data for enhancing psychophysiological coherence. In another example, the user is in a relaxed or psychophysiological coherence state and wants to achieve a mental focused state. In this example the therapeutic data may correspond to the above described therapeutic audios, videos, texts and music for enhancing the mental focused state.

Examples of the third category may comprise examples in which the user does not know his/her present mental state but wants to achieve one of the mental focused state, psychophysiological coherence state, or the relaxed state. The therapeutic audios, videos, texts and music therefore correspond to the respective therapeutic audios, videos, texts and music for enhancing mental focused state, psychophysiological coherence state and relaxed state as described above in the first category.

During listening to the respective therapeutic audios, the digital stethoscope 10, 1000 may measures the effect of the therapeutic data played for this mental state of the user. If the effect is positive, such that the therapeutic data enhance the mental state, no message is output. On the other hand, if no effect is achieved after a certain period of time the digital stethoscope 10, 1000 may output a message: "The selected therapeutic audio is not helpful in achieving the preferred mental state. Please choose another therapeutic audio, video, text or music.". Preferably, the period of time is 30 minutes.

Alternatively, when the user selects to listen only to the heart sound data only the heart sound data are output from the digital stethoscope 10, 1000, wherein the heart sound data work as a psychophysiological coherence enhancing therapeutic data which bring the user into the state of psychophysiological coherence. Next, when the user selects this option, the digital stethoscope 10, 1000 concurrently measures the effect of the own heart sound on the mental state of the user and adjusts the volume of the heart sound to improve the effect.

Alternatively, when the user selects to concurrently listen to the heart beat sound and the therapeutic data, the user can choose between a manual and an automatic mode. In the manual mode the user can choose therapeutic audios, videos, texts and/or music from the same list as in the first option. The user may also determine the respective volumes of the therapeutic audios, videos, texts and music and the heart sound data. Otherwise in the automatic mode, the user may select the mental state he/she wants to achieve. The user may select between mental focused, psychophysiological coherence or relaxed state. After the selection, the controller 60 may automatically select one of the corresponding therapeutic audios, videos, texts and music for enhancing/achieving the mental focused, psychophysiological coherence or relaxed state as described above and may output this therapeutic data concurrently with the heart sound data. Thereby, the controller 60 may concurrently track the effect on the mental state of the user and may adjust volumes of the heart sound and the characteristic of the therapeutic data. If the desired effect is not achieved or not sufficiently achieved in a pre-determined period of time, the digital stethoscope 10, 1000 may automatically change the therapeutic data. Preferably, the predetermined period of time is 30 minutes, but may be set by a user.

To sum up, in light of the above, the therapeutic data such as therapeutic audios, videos, texts and music for achieving the specific mental focused state, psychophysiological coherence state or relaxed state may comprise a combination of different kinds of therapeutic data.

Advantageous Therapeutic Effect

The hereinabove described embodiments of the physiological data monitoring device 10 in form of the digital stethoscope 10, 1000 of the present invention provides the following therapeutic effect. The digital stethoscope 10, 1000 of the present invention enables simultaneous listening to a person's own heart and therapeutic texts or suggestions. This has an advantage in psychological, psychotherapeutic treatment of a patient and in increasing the self-conscious and overall personal well-being. Listening to her/his own heartbeat works hypnotically and subconsciously brings everyone back to the beginning of her/his life; as the developing baby under the mother's heart everyone first hears (and listens to all subsequent pregnancies) the very voice of mother's heart beating. In addition to relaxation and increased suggestibility/openness while listening to personal heart rhythms, therapeutic texts and suggestions address the complex mechanisms of the psyche and activate the individual's unconscious sources of power and support the body's healing processes. In the hypnotically altered state of consciousness, which eventually appears when listening to one's own heart, and with appropriate therapeutic suggestions, we can bypass the otherwise well-established and realistic, but also inhibiting notions of the conscious mind. Therapeutic suggestions allow the imagination and encourage it to seek solutions for themselves and in their own way, even beyond the established known frameworks. In this way, they push the boundaries of the realistically possible and in a mysterious way activate the doctor in each individual. Various therapeutic texts and suggestions allow an individual to simply relax and calm down or rest in harmony with their own heart rhythm, or guided meditation, or invaluable support and activation of still non-functioning healing processes of the body in the treatment of various disorders and diseases.

The invention claimed is:

1. A digital stethoscope, comprising:
a housing;
a physiological data acquisition unit configured to acquire a signal comprising a heart sound data, the physiological data acquisition unit comprising a detection unit and a processing unit, wherein the processing unit is configured to process the signal detected in the detection unit for improving a quality of the signal;
a therapeutic data unit providing a therapeutic data, the therapeutic data unit comprising a memory unit configured to store the therapeutic data;
an output unit configured to output heart sound data and therapeutic data;
a communication unit configured to receive the therapeutic data from an external device; and
a controller being connected to the physiological data acquisition unit to receive heart sound data, the controller is further connected to the therapeutic data unit to receive the therapeutic data from the therapeutic data unit and the controller is connected to the output unit to output heart sound data and therapeutic data,
wherein the physiological data acquisition unit, the controller, and the therapeutic data unit are provided within the housing,
wherein the controller is configured to automatically select therapeutic data for being output based on the acquired heart sound data,
wherein the therapeutic data comprises a therapeutic audio text selected by a user on the external device to improve or enhance or influence the physical and/or mental state of the user, the therapeutic audio text comprising text modules that motivate the user, focus the user, relax the user, bring psychophysiological coherence to the user, or any combination thereof,
wherein the heart sound data and the therapeutic data are simultaneously outputted by the output unit, the output unit being a loudspeaker or an earphone, and
wherein during the listening to the therapeutic audio text, the controller is configured to determine an effect of the therapeutic audio text played for a present mental state of the user, and, if the controller determines that an effect is not achieved after a preset period of time, the digital stethoscope is configured to output a message.

2. The digital stethoscope of claim 1, wherein the communication unit is further configured to receive and/or transfer physiological data from or to an external device and/or transfer the therapeutic data to the external device.

3. The digital stethoscope of claim 1, wherein the physical data acquisition unit comprises at least one of:
a detection unit configured to detect a heart sound data,
a processing unit configured to process the heart sound data,
a communication unit configured to transfer heart sound data to an external device, and
a memory unit for storing at least part of the heart sound data.

4. The digital stethoscope of claim 1, wherein the therapeutic data unit comprises at least one of:
a memory unit for storing the therapeutic data, and/or
a communication unit capable of transmitting and/or receiving the therapeutic data to an external device and/or from an external device.

5. The digital stethoscope of claim 1, wherein the therapeutic data further comprises at least one of:
a therapeutic text,
a therapeutic video,
a therapeutic instruction, and
a proposal of a medical treatment and a combination thereof.

6. The digital stethoscope of claim 1, wherein the digital stethoscope is configured to:
acquire the signal including heart sound data,
determine a signal value of the acquired signal,
compare the determined signal value of the acquired signal with a predetermined threshold value,
if the determined signal value is higher than the predetermined threshold value, output a control signal indicating that the digital stethoscope is in an appropriate position for acquiring heart sound data, and
if the determined signal value is lower than the predetermined threshold value, output a control signal indicating that the digital stethoscope is not in an appropriate position for acquiring heart sound data.

7. The digital stethoscope of claim 6, wherein the digital stethoscope is further configured to continue acquiring heart sound data, after it has been determined that the digital stethoscope is in an appropriate position for acquiring heart sound data.

8. The digital stethoscope of claim 7, wherein when the digital stethoscope is not in an appropriate position for acquiring the heart sound data, the digital stethoscope is configured to output a signal comprising positioning instructions on how to position the digital stethoscope and/or the physiological data acquisition unit to achieve an appropriate position for acquiring the heart sound data.

9. The digital stethoscope of claim 8, wherein the positioning instructions are based on an acquired signal comprising heart sound data.

10. The digital stethoscope of claim 1, wherein the housing of the digital stethoscope comprises:

a bottom portion, a middle portion provided on the bottom portion, and a top portion provided on the middle portion.

11. The digital stethoscope of claim 10, wherein a radius of the bottom portion is greater than a radius of the top portion, and/or the middle portion is formed as a bell shape, wherein the radius of an upper part of the bell-shaped middle portion is smaller than a lower part of the bell-shaped middle portion; and/or a neck-shaped portion is provided between the bell-shaped middle portion and the top portion, and the neck-shaped portion has a radium being smaller than the upper radius of the bell-shaped middle portion.

12. The digital stethoscope of claim 10, wherein the physiological data acquisition unit is provided in the bottom portion or is connected to the bottom portion.

13. The digital stethoscope of claim 10, wherein the top portion comprises a flat portion being substantially parallel to a bottom surface of the bottom portion.

14. The digital stethoscope of claim 10, wherein the therapeutic data unit is provided in the middle portion.

15. The digital stethoscope of claim 10, wherein the top portion comprises an input unit and/or the output unit.

16. The digital stethoscope of claim 1, wherein the controller is configured to select therapeutic data for being output at least based on heart sound data acquired by the physiological data acquisition unit and on data input by a user.

17. The digital stethoscope of claim 1, wherein the therapeutic data is output by the output unit before the heart sound data is output or the heart sound data is output by the output unit before the therapeutic data is output.

18. A system comprising the digital stethoscope and an external device communicating with the digital stethoscope, wherein the digital stethoscope comprises:

a housing;

a physiological data acquisition unit configured to acquire a heart sound data, the physiological data acquisition unit comprising a detection unit and a processing unit, wherein the processing unit is configured to process the signal detected in the detection unit for improving a quality of the signal;

a therapeutic data unit providing a therapeutic data, the therapeutic data unit comprising a memory unit configured to store the therapeutic data;

an output unit configured to output heart sound data and therapeutic data;

a communication unit configured to receive the therapeutic data from an external device; and a controller being connected to the physiological data acquisition unit to receive heart sound data, the controller is further connected to the therapeutic data unit to receive the therapeutic data from the therapeutic data unit and the controller is connected to the output unit to output heart sound data and therapeutic data, wherein the physiological data acquisition unit, the controller, and the therapeutic data unit are provided within the housing, wherein the controller is configured to automatically select therapeutic data for being output based on the acquired heart sound data, wherein the therapeutic data comprises a therapeutic audio text that is selected by a user on the external device and configured to improve, enhance, or influence the physical and/or mental state of a user, the therapeutic audio text comprising text modules that motivate the user, focus the user, relax the user, bring psychophysiological coherence to the user, or any combination thereof, wherein the heart sound data and the therapeutic data are simultaneously outputted by the output unit, the output unit being a loudspeaker or an earphone, wherein during the listening to the therapeutic audio text, the controller is configured to determine an effect of the therapeutic audio text played for a present mental state of the user, and, if the controller determines that an effect is not achieved after a preset period of time, the digital stethoscope is configured to output a message; and wherein the external device further comprises:

a communication unit configured to communicate with the digital stethoscope; and a storage unit for storing the heart sound data and/or the therapeutic data.

\* \* \* \* \*